(12) United States Patent
Yin et al.

(10) Patent No.: US 11,511,983 B2
(45) Date of Patent: Nov. 29, 2022

(54) LIQUID COLLECTING DEVICE

(71) Applicant: LINKGEN BIOTECH SHANGHAI CO., LTD., Shanghai (CN)

(72) Inventors: Zhongqi Yin, Shanghai (CN); Weiwei Li, Shanghai (CN); Liqing Xu, Shanghai (CN); Jin Pan, Shanghai (CN)

(73) Assignee: LINKGEN BIOTECH SHANGHAI CO., LTD., Shanghai (CN)

( * ) Notice: Subject to any disclaimer, the term of this patent is extended or adjusted under 35 U.S.C. 154(b) by 400 days.

(21) Appl. No.: 16/760,611

(22) PCT Filed: Dec. 24, 2019

(86) PCT No.: PCT/CN2019/127916
§ 371 (c)(1),
(2) Date: Apr. 30, 2020

(87) PCT Pub. No.: WO2020/186869
PCT Pub. Date: Sep. 24, 2020

(65) Prior Publication Data
US 2021/0070598 A1    Mar. 11, 2021

(30) Foreign Application Priority Data

Mar. 18, 2019   (CN) .......................... 201910205969.5

(51) Int. Cl.
*B67C 11/02* (2006.01)
*A61B 10/00* (2006.01)

(52) U.S. Cl.
CPC .......... *B67C 11/02* (2013.01); *A61B 10/0051* (2013.01)

(58) Field of Classification Search
CPC ......... A61B 10/00; A61J 19/00; G01N 33/48; G01N 1/34
USPC .............................................. 4/258; 232/43.1
See application file for complete search history.

(56) References Cited

U.S. PATENT DOCUMENTS 4,768,238 A * 9/1988 Kleinberg .......... A61B 10/0051
4/144.1
2010/0331725 A1* 12/2010 Libby ................ A61B 10/0051
600/573

FOREIGN PATENT DOCUMENTS

| CN | 106644602 | * | 5/2017 | ............... G01N 1/20 |
| WO | WO1999/06827 | * | 2/1999 | ............. G01N 33/48 |

* cited by examiner

*Primary Examiner* — Walter E Webb
(74) *Attorney, Agent, or Firm* — Workman Nydegger

(57) ABSTRACT

Provided is a liquid collecting device, which comprises a collecting container, wherein the collecting container is provided with a diversion cavity for diverting a body fluid collected; on a wall of the collecting container, at least one jacket cavity configured to store a storage liquid is provided, the jacket cavity is provided around the diversion cavity, and the jacket cavity extends along an axial direction of the diversion cavity, and a cross section of the jacket cavity is annular; and the diversion cavity has an inflow port and an outflow port, and an aperture of the inflow port is larger than that of the outflow port.

20 Claims, 13 Drawing Sheets

LIQUID COLLECTING DEVICE

CROSS-REFERENCE TO RELATED APPLICATION

The present disclosure claims the priority to the Chinese patent application with the filing number 2019102059695 filed with the Chinese Patent Office on Mar. 18, 2019 and entitled "Liquid Collecting Device".

TECHNICAL FIELD

The present disclosure relates to the technical field of liquid collection, and particularly to a liquid collecting device.

BACKGROUND ART

In the existing liquid collecting devices, for example, body fluid collecting devices, various components such as a funnel, a collecting tube and a container containing a storage liquid of a split type saliva collector, specifically, for collecting saliva are independently provided. In use, saliva is spit first, then a container lid of a container that contains a storage liquid is opened, the storage liquid is poured into the collecting tube through the funnel, then the funnel is taken off, and a lid that is separately provided is screwed on. Thus, the whole operation is relatively tedious.

SUMMARY

The present disclosure aims at, for example, providing a liquid collecting device, so as to overcome, to some extent, the technical problem of relatively tedious body fluid collecting operation existing in the prior art.

Embodiments of the present disclosure are realized as follows:
the present disclosure provides a liquid collecting device, which includes a collecting container, wherein the collecting container is provided with a diversion cavity for diverting a body fluid collected; on a wall of the collecting container, at least one jacket cavity configured to store a storage liquid is provided, the jacket cavity is provided around the diversion cavity, and the jacket cavity extends along an axial direction of the diversion cavity, and a cross section of the jacket cavity is annular; and the diversion cavity has an inflow port and an outflow port, and an aperture of the inflow port is larger than that of the outflow port.

Optionally, an inner diameter of the diversion cavity gradually decreases in a direction from the inflow port to the outflow port.

Optionally, the number of the jacket cavity is plural, and the plurality of jacket cavities are independent from each other.

Optionally, the liquid collecting device further includes an isolation layer, the plurality of jacket cavities are separated by the isolation layer, and a length of the isolation layer extends along an axial direction of the diversion cavity; and the isolation layer is in a cylindrical shape (skirt like shape or flared shape).

Optionally, the plurality of jacket cavities are sequentially sleeved from inside to outside along a radial direction of the diversion cavity, a wall surface of an innermost one of the jacket cavities is opposite to an inner wall surface of the diversion cavity, wherein the innermost one of the jacket cavities is isolated from the diversion cavity by a chamber separation layer.

Optionally, the liquid collecting device further includes a storing container, and the storing container is connected to the collecting container, and it is configured that the diversion cavity is communicated with an accommodating cavity of the storing container.

Optionally, the number of the jacket cavity is 1.

Optionally, the storing container is movably connected to the collecting container, such that the jacket cavity is communicated with or disconnected from the accommodating cavity of the storing container.

Optionally, the storing container is rotationally connected to the collecting container, such that the jacket cavity is communicated with or disconnected from the accommodating cavity of the storing container.

Optionally, the storing container is in threaded connection with the collecting container, such that the jacket cavity is communicated with or disconnected from the accommodating cavity of the storing container.

Optionally, the collecting container has an insertion portion configured to be inserted into the storing container; the insertion portion and an inner wall of the storing container have a communicated state therebetween, in which the storage liquid stored in the jacket cavity is enabled to flow into the accommodating cavity of the storing container; the insertion portion and the inner wall of the storing container further have a disconnected state therebetween, in which the storage liquid is sealed in the jacket cavity.

Optionally, an inner circumferential wall of the insertion portion is configured to form a part of a wall surface of the diversion cavity; an outer circumferential wall of the insertion portion is configured to form a part of a wall surface of the jacket cavity; the outer circumferential wall of the insertion portion is attached to the inner wall of the storing container so as to realize sealing.

Optionally, the collecting container further includes an inner shell portion, a capping portion and an outer shell portion, an inner wall of the inner shell portion defines the diversion cavity, and an end of the inner shell portion forming the outflow port is connected to the insertion portion; the capping portion is annular, an end of the inner shell portion forming the inflow port is connected to an inner ring (inner edge) of the capping portion, the outer shell portion is connected to an outer ring (outer edge) of the capping portion, an extending direction of the outer shell portion is consistent with an extending direction of the inner shell portion; and an end of the outer shell portion away from the capping portion protrudes beyond the insertion portion; and the outer shell portion, the capping portion and the inner shell portion jointly define the jacket cavity.

Optionally, the outer shell portion includes a variable-diameter shell section and a constant-diameter shell section, an inner diameter of the variable-diameter shell section gradually decreases from one end close to the capping portion to the other end, an end of the constant-diameter shell section is connected to an end of the variable-diameter shell section away from the capping portion, an end of the constant-diameter shell section away from the variable-diameter shell section protrudes beyond the insertion portion, and a to-be-sealed region is formed between the constant-diameter shell section and the variable-diameter shell section; the storing container is movable relative to the collecting container, such that the storing container is able to locate in the sealed region (i.e., to-be-sealed region) so as to block the jacket cavity from the accommodating cavity of the storing container, and such that the storing container is able to separate from the sealed region so as to communicate the jacket cavity with the accommodating cavity of the storing container.

Optionally, the storing container includes a container body and a sleeve-shaped structure sleeved outside the container body, an annular grove configured to accommodate the constant-diameter shell section is formed between the container body and the sleeve-shaped structure; the constant-diameter shell section is in threaded connection with the sleeve-shaped structure, the container body is configured to move to be located in the sealed region so as block the jacket cavity from the accommodating cavity of the storing container, and move to be separated from the sealed region so as to communicate the jacket cavity with the accommodating cavity of the storing container.

Optionally, the liquid collecting device further includes a sealing element, and the sealing element is provided between the container body and the insertion portion, and configured to seal a gap between the container body and the insertion portion.

Optionally, the insertion portion is provided with a bending section that is bent away from the diversion cavity, the bending section is provided with a liquid outlet, the storing container is capable of opening or blocking the liquid outlet, and when the liquid outlet is opened by the storing container, the jacket cavity, the liquid outlet and the accommodating cavity of the storing container are communicated in sequence; and when the liquid outlet is blocked by the storing container, the jacket cavity is blocked from the accommodating cavity of the storing container.

Optionally, the storing container is provided with a spherical protrusion configured to block the liquid outlet.

Optionally, the liquid collecting device further includes a sealing film connected to the collecting container, and the sealing film is configured to seal the storage liquid in the jacket cavity.

Optionally, a sealing separator is installed in the storing container; a blocking hole is provided in the sealing separator; the sealing separator divides the accommodating cavity of the storing container into an upper sealed cavity and a lower sealed cavity, the upper sealed cavity is configured to be communicated with the diversion cavity, and the storage liquid is pre-stored in the lower sealed cavity; the collecting container is connected to a connecting rod, an end portion of the connecting rod is connected to a sealing block, and the sealing block is capable of being inserted into the blocking hole, so as to block the blocking hole.

Compared with the prior art, beneficial effects of the embodiments of the present disclosure include, for example: the liquid collecting device provided in the present disclosure includes the collecting container, wherein the collecting container is provided with the diversion cavity for diverting the body fluid collected; on the wall of the collecting container, at least one jacket cavity configured to store a storage liquid is provided, the jacket cavity is provided around the diversion cavity, and the jacket cavity extends along the axial direction of the diversion cavity; and the diversion cavity has the inflow port and the outflow port, and the aperture of the inflow port is larger than that of the outflow port. By means of the diversion cavity, it is convenient to divert the liquid (e.g., saliva, blood or urine) to be collected, meanwhile, at least one jacket cavity is provided, the storage liquid is stored in the collecting container, so that the collecting container has dual functions of diverting the liquid and storing the storage liquid. Thus in use, a container (e.g. collecting tube) separately storing the storage liquid is omitted, the operation is simplified, the efficiency is improved, and the cost is reduced.

BRIEF DESCRIPTION OF DRAWINGS

In order to more clearly illustrate technical solutions of embodiments of the present disclosure or the prior art, accompanying drawings which need to be used in the description of the embodiments or the prior art will be introduced briefly below. It should be understood that the accompanying drawings below merely show some embodiments of the present disclosure, therefore, they should not be considered as limitation on the scope, and a person ordinarily skilled in the art still could obtain other relevant accompanying drawings according to these accompanying drawings, without using creative efforts.

DETAILED DESCRIPTION OF EMBODIMENTS

Figure 1:
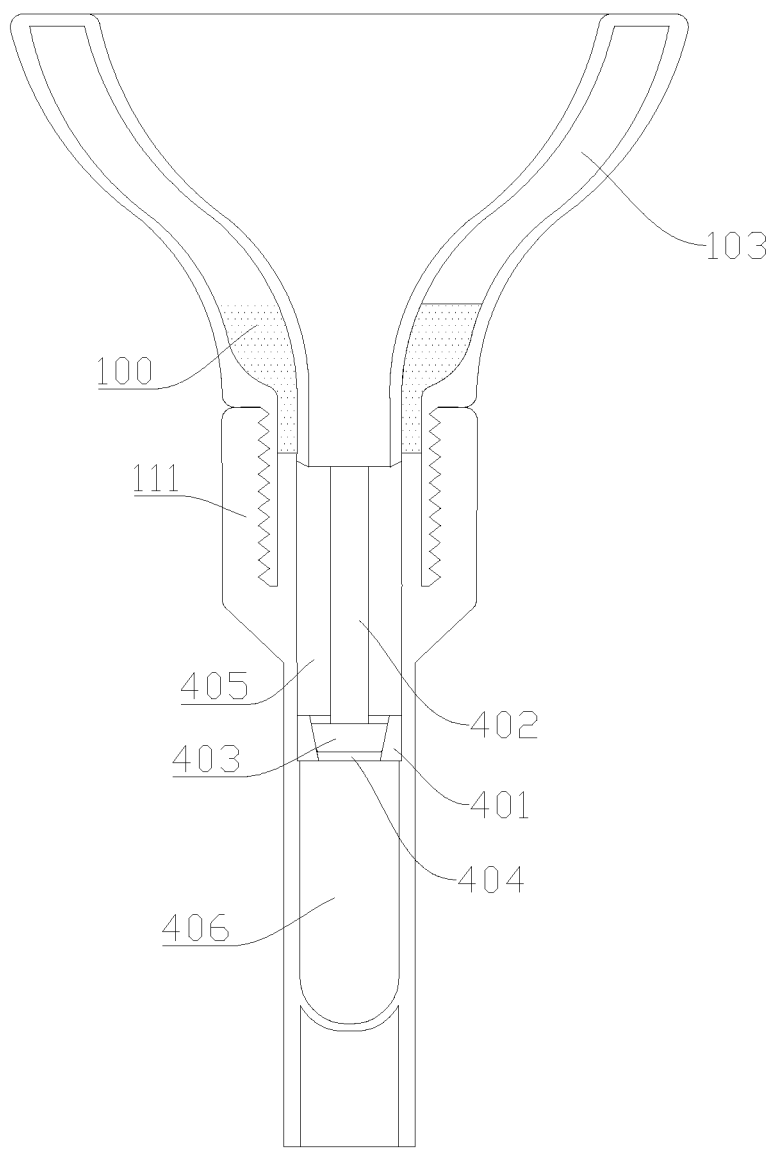
FIG. 1 is a structural schematic diagram (cutaway view) of a liquid collecting device provided in an embodiment of the present disclosure.
Figure 2:
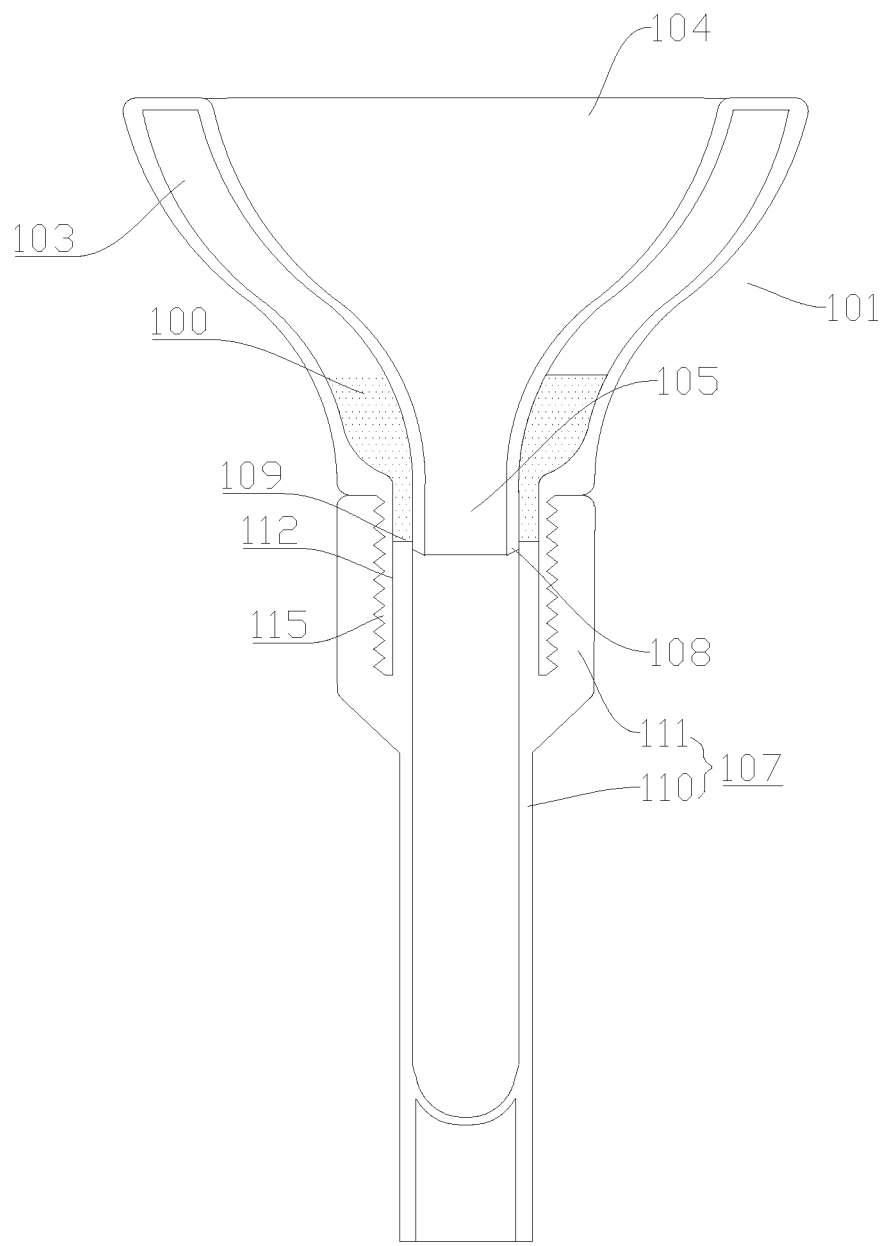
FIG. 2 is a schematic diagram (cutaway view) of another modified structure of the liquid collecting device provided in an embodiment of the present disclosure.
Figure 3:
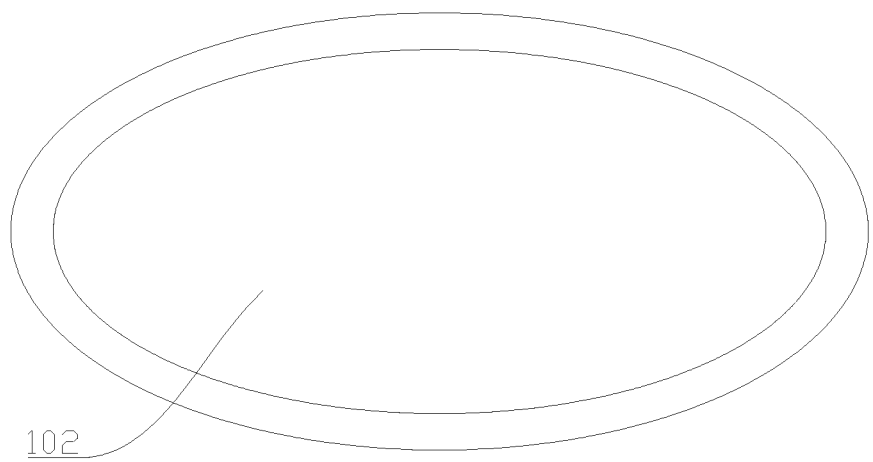
FIG. 3 is a top view of a collecting container of the liquid collecting device shown in FIG. 2.

In order to make objects, technical solutions and advantages of the embodiments of the present disclosure clearer, below the technical solutions in the embodiments of the present disclosure will be described clearly and completely in conjunction with the accompanying drawings in the embodiments of the present disclosure, and apparently, some but not all embodiments of the present disclosure are described. Generally, components in the embodiments of the present disclosure described and shown in the accompanying drawings herein can be arranged and designed in various different configurations.

Therefore, the detailed description of the embodiments of the present disclosure provided in the accompanying drawings below is not intended to limit the scope of the present disclosure claimed, but merely represents chosen embodiments of the present disclosure. Based on the embodiments in the present disclosure, all other embodiments obtained by those ordinarily skilled in the art without using creative efforts shall fall within the scope of protection of the present disclosure.

It should be noted that similar reference signs and letters represent similar items in the following accompanying drawings, therefore, once a certain item is defined in one accompanying drawing, it does not need to be further defined or explained in subsequent accompanying drawings.

In the description of the present disclosure, it should be noted that orientational or positional relationships indicated by terms such as "upper", "lower", "vertical", "horizontal", "inner", and "outer" are based on orientational or positional relationships as shown in the accompanying drawings, or orientational or positional relationships of a product of the present disclosure when being conventionally placed in use, merely for facilitating describing the present disclosure and simplifying the description, rather than indicating or implying that related devices or elements have to be in the specific orientation or configured and operated in a specific orientation, therefore, they should not be construed as limiting the present disclosure.

Besides, terms such as "first" and "second", if appear, are merely used for distinctive description, but should not be construed as indicating or implying relative importance.

Moreover, terms such as "horizontal", "vertical", and "pendulous", if appear, do not mean that a component is required to be absolutely horizontal or pendulous, but mean that the component can be slightly inclined. For example, by "horizontal" it merely means that a structure is more horizontal in comparison with "vertical", rather than being completely horizontal, while the structure can be slightly inclined.

In the description of the present disclosure, it also should be noted that unless otherwise specified and defined clearly, terms "provide", "mount", "join", and "connect", if appear, should be understood in a broad sense, for example, a connection can be a fixed connection, a detachable connection, or an integrated connection; it can be a mechanical connection or an electrical connection; it can be a direct connection or an indirect connection through an intermediate medium, and it also can be an inner communication between two elements. For a person ordinarily skilled in the art, specific meanings of the above-mentioned terms in the present disclosure can be understood according to specific circumstances.

It should be noted that the features in the present disclosure may be combined with each other if there is no conflict.

Referring to what is shown in FIG. 2, FIG. 3, FIG. 12, FIG. 13 and FIG. 14, the present disclosure provides a liquid collecting device, which includes a collecting container 101, the collecting container 101 is provided with a diversion cavity 102 for diverting a liquid (not shown in the drawings) to be collected and at least one jacket cavity 103 configured to store a storage liquid 100, the jacket cavity 103 is provided on a wall of the collecting container 101, the jacket cavity 103 is provided around the diversion cavity 102, and the jacket cavity 103 extends along an axial direction of the diversion cavity 102, that is to say, an axial direction of the jacket cavity 103 is substantially parallel to the axial direction of the diversion cavity 102; the diversion cavity 102 has an inflow port 104 and an outflow port 105, and an aperture of the inflow port 104 is larger than that of the outflow port 105; and a diameter of a cross-sectional profile of the diversion cavity 102 gradually decreases in a direction from the inflow port 104 to the outflow port 105.

Specifically, the cross-sectional profile of the jacket cavity 103 is annular, that is to say, the radial cross-sectional profile of the jacket cavity 103 is annular, in other words, the cross-sectional profile of the jacket cavity 103 perpendicular to the axial direction thereof is annular, so that the jacket cavity 103 is provided around the diversion cavity 102. In the present disclosure, the number of the jacket cavity 103 being 1 is taken as an example to make specific illustration, and the jacket cavity 103 has a liquid outlet 109 that can be opened or closed. The collecting container 101 may be a structure in a funnel shape, and in use, the liquid (e.g., saliva, blood or urine) flows in through the inflow port 104 of the diversion cavity 102, and flows out through the outflow port 105 of the diversion cavity 102. It should be noted that the number of the jacket cavity 103 may also be 2~6.

The liquid collecting device provided in the present disclosure is provided with the diversion cavity 102 and the jacket cavity 103, the liquid (e.g., saliva, blood or urine) is diverted by the diversion cavity 102, and the storage liquid 100 is stored in at least one jacket cavity 103, so that the collecting container 101 has dual functions of diverting the liquid and storing the storage liquid 100, and in use, a container (e.g. collecting tube) separately configured to store the storage liquid 100 is omitted, thus simplifying the operation, improving the efficiency, and reducing the cost.

In the present disclosure, the liquid collecting device 101 further includes a storing container 107, and the storing container 107 is connected to the collecting container 101, so that the diversion cavity 102 is communicated with an accommodating cavity 1102 of the storing container 107. In use, the liquid to be collected enters the diversion cavity 102 through the inflow port 104 of the diversion cavity 102 of the collecting container 101, the diversion cavity 102 of the collecting container 101 diverts the liquid from the outflow port 105 of the diversion cavity 102 into the storing container 107, and meanwhile, when the liquid outlet 109 of the jacket cavity 103 is opened, the storage liquid 100 in the jacket cavity 103 can enter the storing container 107 through the liquid outlet 109, and after the storage liquid 100 in the jacket cavity 103 flows into the storing container 107, mixing of the body fluid with the storage liquid 100 is realized in the storing container 107.

Optionally, the material of the collecting container 101 and the material of the storing container 107 may both include transparent materials, for example, transparent plastics or transparent glass. In other words, the collecting container 101 and the storing container 107 may both be made of transparent materials (for example, transparent plastics or transparent glass).

In the present disclosure, the storing container 107 is in threaded connection with the collecting container 101. In other words, the connection between the storing container 107 and the collecting container 101 is realized by a threaded connection structure.

In the present disclosure, the collecting container 101 is provided with an external thread, and the storing container 107 is provided with an internal thread that fits the external thread on the collecting container 101. When the liquid outlet 109 of the jacket cavity 103 is opened, the jacket cavity 103 is communicated with the accommodating cavity 1102 of the storing container 107, and the storage liquid 100 can directly enter the storing container 107.

In the present disclosure, one of the storing container 107 and the collecting container 101 is rotated relatively to the other so as to communicate or disconnect the jacket cavity 103 with or from the accommodating cavity 1102 of the storing container 107. Through relative rotation of one of the storing container 107 and the collecting container 101 relative to the other in a first direction, the liquid outlet 109 of the jacket cavity 103 is opened, such that the jacket cavity 103 is communicated with the accommodating cavity 1102 of the storing container 107, thus the storage liquid 100 in the jacket cavity 103 can conveniently flow into the accommodating cavity 1102 of the storing container 107; and through relative rotation of one of the storing container 107 and the collecting container 101 relative to the other in a second direction opposite to the first direction, the liquid outlet 109 of the jacket cavity 103 is blocked, such that the jacket cavity 103 is blocked from the accommodating cavity 1102 of the storing container 107, and the storage liquid 100 located in the jacket cavity 103 cannot flow into the accommodating cavity 1102 of the storing container 107 through the liquid outlet 109 of the jacket cavity 103. It should be noted that the communication can be realized by rotating the storing container 107 counterclockwise relative to the collecting container 101, and the disconnection can be realized by rotating the storing container 107 clockwise relative to the collecting container 101. In other words, the first direction may be a counterclockwise direction when the liquid collecting device is in use, and the second direction may be a clockwise direction when the liquid collecting device is in use.

In the present disclosure, the collecting container 101 has an insertion portion 108 configured to be inserted into the storing container 107; an outer diameter of the insertion portion 108 is smaller than an inner diameter of the storing container, and the insertion portion 108 and an inner wall of the storing container 107 have a communicated state therebetween, in which the storage liquid 100 stored in the jacket cavity 103 is enabled to flow into the accommodating cavity 1102 of the storing container 107; the insertion portion 108 and the inner wall of the storing container 107 further have a disconnected state therebetween, in which the storage liquid is sealed in the jacket cavity 103.

Specifically, an inner circumferential wall of the insertion portion 108 is configured to form a wall surface of the diversion cavity 102, and an outer circumferential wall of the insertion portion 108 is configured to form a wall surface of the jacket cavity 103; an outer circumferential wall of the insertion portion 108 and an inner wall of the storing container 107 can be attached to each other so as to realize sealing. When the collecting container 101 is far away from the storing container 107, the insertion portion 108 gradually comes out of the storing container 107, and the liquid outlet 109 of the jacket cavity 103 is opened, so that the storage liquid 100 stored in the jacket cavity 103 flows into the accommodating cavity 1102 of the storing container 107. When the collecting container 101 approaches the storing container 107, and when the insertion portion 108 gradually extends into the storing container 107, the liquid outlet 109 of the jacket cavity 103 is blocked, so that the storage liquid 100 is sealed inside the jacket cavity 103.

Figure 10:
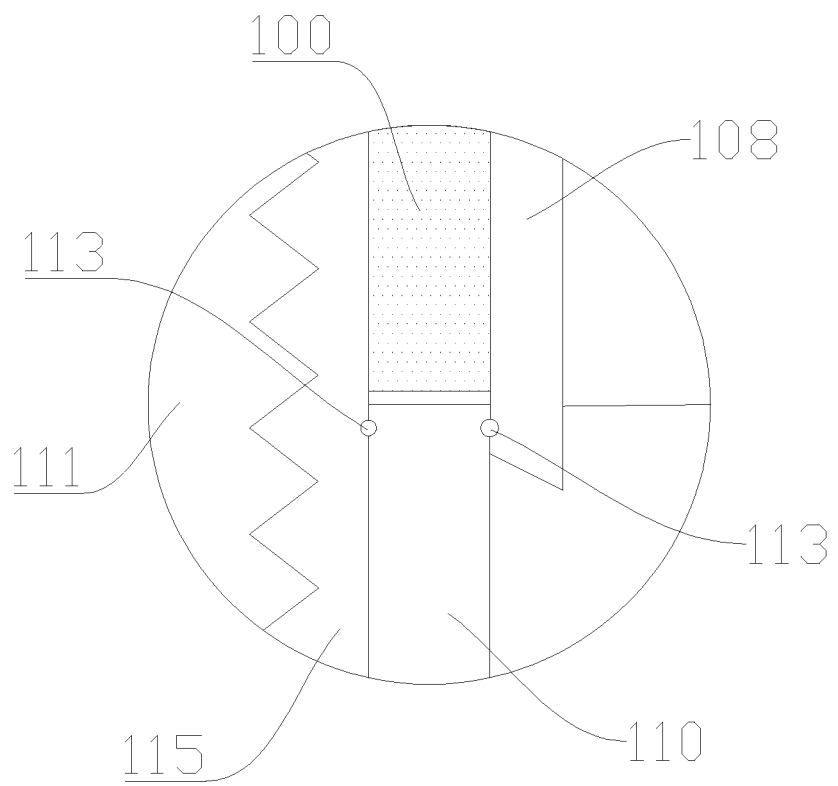
FIG. 10 is a partially enlarged schematic diagram of part B in FIG. 9.

Please referring to FIG. 10, optionally, the insertion portion 108 may be of a tubular structure. It should be noted that an annular groove 112 can be provided on an inner wall of the storing container 107, a sealing element, which may be a sealing ring 113, is installed in the annular groove 112, and when the insertion portion 108 extends into the storing container 107, the sealing ring 113 is sleeved outside the insertion portion 108, thus further ensuring the sealing performance between the outer circumferential wall of the insertion portion 108 and the inner wall of the storing container 107, and preventing the storage liquid 100 in the jacket cavity 103 from leaking when the liquid outlet 109 is in the disconnected state. In other words, when the liquid outlet 109 of the jacket cavity 103 is in the disconnected state, the storage liquid 100 is kept in a state of being stored in the jacket cavity 103, and does not flow out through the liquid outlet 109, and by additionally providing the sealing ring 113, the sealing performance between the outer circumferential wall of the insertion portion 108 and the inner wall of the storing container 107 is improved, and the storage liquid 100 located inside the jacket cavity 103 is not easy to leak.

Optionally, the sealing ring 113 may be an O-shaped sealing ring.

In the present disclosure, the storing container 107 includes a container body 110 and a sleeve-shaped structure 111 located outside the container body 110, the internal thread on the storing container 107 is located on the shell-shaped structure 111, and the sleeve-shaped structure 111 is connected to the collecting container 101. In other words, the threaded connection between the storing container 107 and the collecting container 101 is realized.

Specifically, the sleeve-shaped structure 111 includes an inner circumferential wall and an annular inner bottom wall, the inner circumferential wall is connected to the inner bottom wall, the inner circumferential wall extends around the circumference of the inner bottom wall, the inner circumferential wall, the inner bottom wall and an outer circumferential wall at a container mouth of the container body 110 jointly form the annular groove 112, the internal thread is located in the annular groove 112, and located on the inner circumferential wall of the sleeve-shaped structure 111. After the collecting container 101 is in threaded connection with the internal thread, an outer shell portion 115 of the collecting container 101 having the external thread enters the annular groove 112, thus the outer shell portion, a top end surface of the container mouth of the container body 110 of the storing container 107 and the insertion portion 108 together realize the sealing of the liquid outlet 109 of the jacket cavity 103. Through the cooperation of the sleeve-shaped structure 111, the outer shell portion 115, the insertion portion 108 and the threaded connection between the storing container 107 and the collecting container 101, the function of communicating or disconnecting the jacket cavity 103 with or from the accommodating cavity 1102 of the storing container 107 is realized upon relative rotation between the storing container 107 and the collecting container 101.

Figure 8:
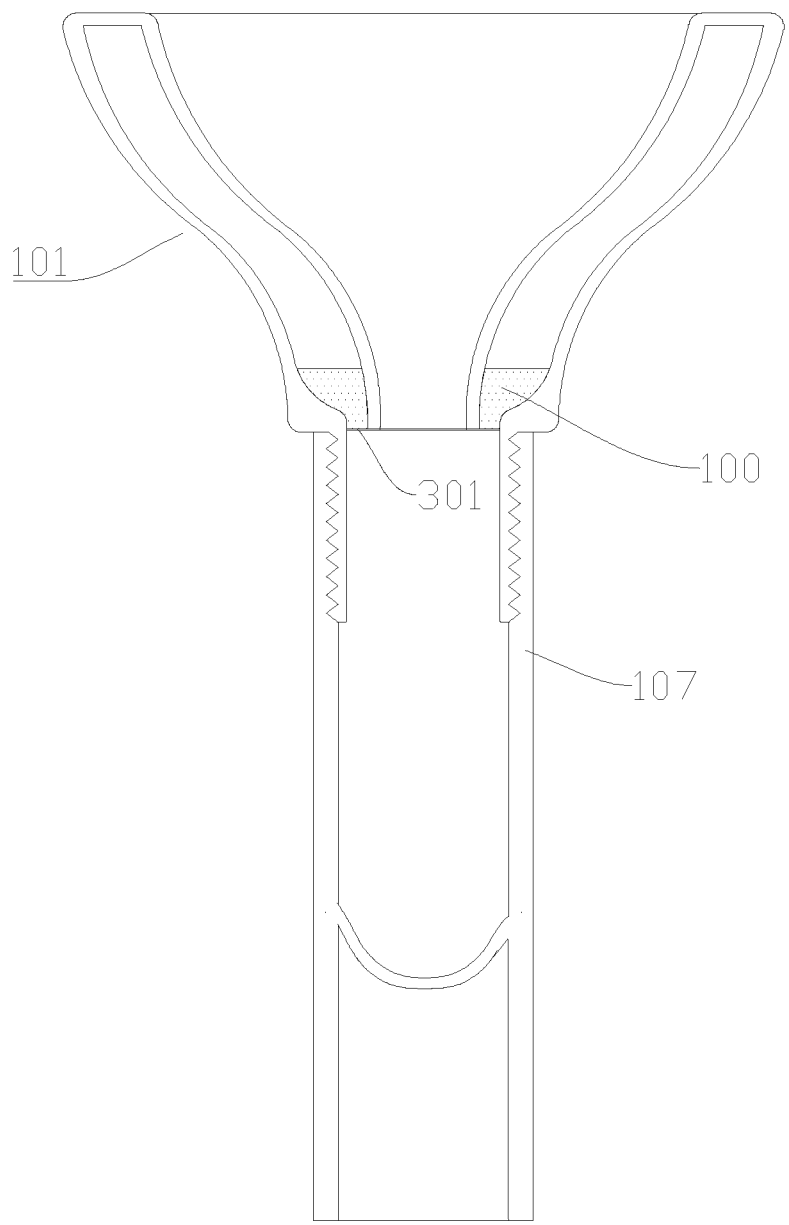
FIG. 8 is a schematic diagram (cutaway view) of another modified structure of the liquid collecting device provided in an embodiment of the present disclosure.
Figure 9:
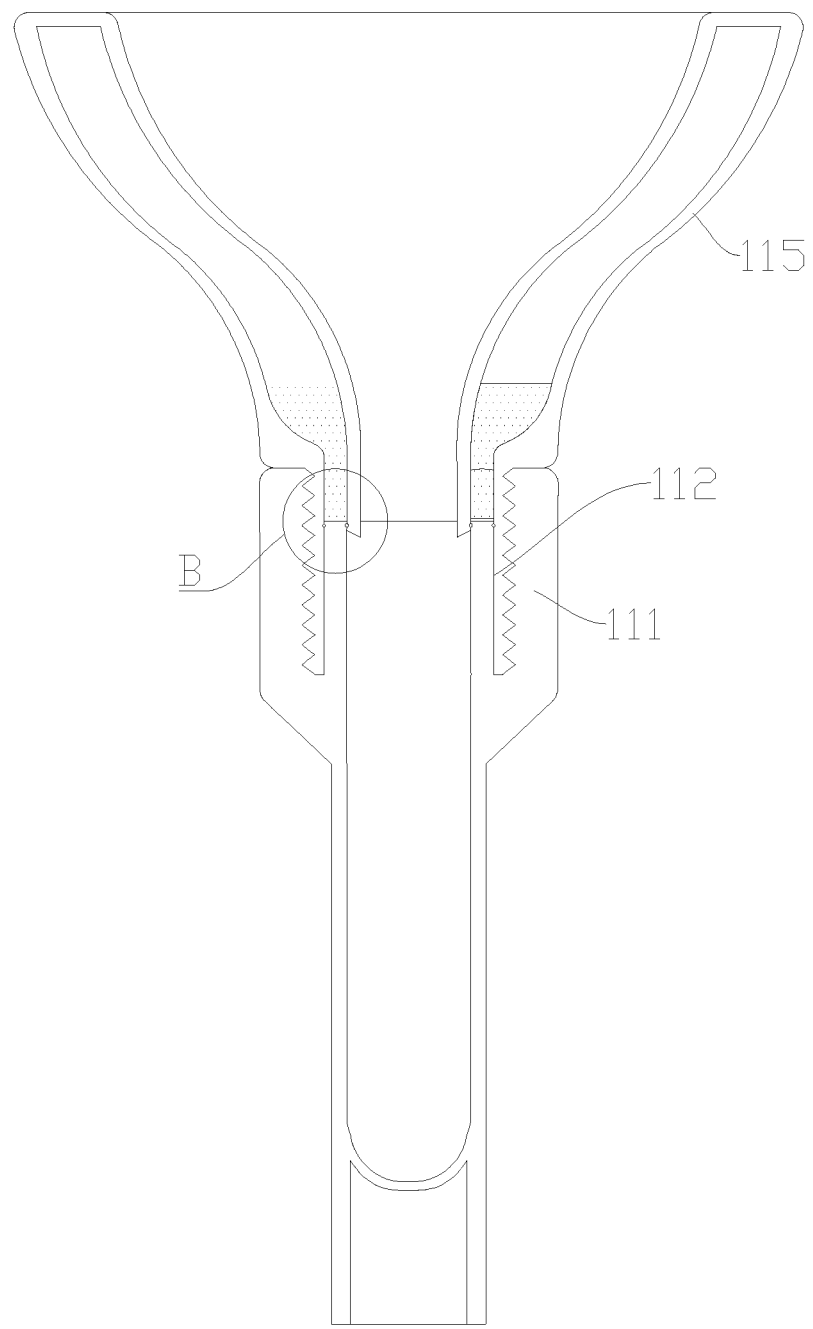
FIG. 9 is a schematic diagram (cutaway view) of another modified structure of the liquid collecting device provided in an embodiment of the present disclosure.

It should be noted that, referring to what is shown in FIG. 8 and FIG. 9, an annular groove 112 can be provided on an outer wall of the container body 110, a sealing ring 113 is installed in the annular groove 112, and when the outer shell portion 115 extends into the annular groove 112, the sealing ring 113 is located between the outer shell portion 115 and the inner circumferential wall of the sleeve-shaped structure 111. In other words, the sealing ring 113 is sleeved outside the container body 110, thus further ensuring the sealing performance between the inner circumferential wall of the outer shell portion 115 and the outer wall of the container body 110, and preventing the storage liquid 100 in the jacket cavity 103 from leaking when the liquid outlet 109 is in the disconnected state. Optionally, the sealing ring 113 may be an O-shaped ring. In order to meet the requirement of large-scale batch production in a laboratory, the outer circumferential wall of the bottom portion of the storing container 107 can be provided with ridges or recesses in a circumferential direction, and the outer circumferential wall of the collecting container 101 can be provided with ridges or grooves, so as to facilitate cooperation with an automatically started machine; in addition, the bottom portion of the storing container 107 further can be designed with a laser engraved or bonded two-dimensional code, so that management of sample libraries such as code scanning classification can be facilitated.

Figure 15:
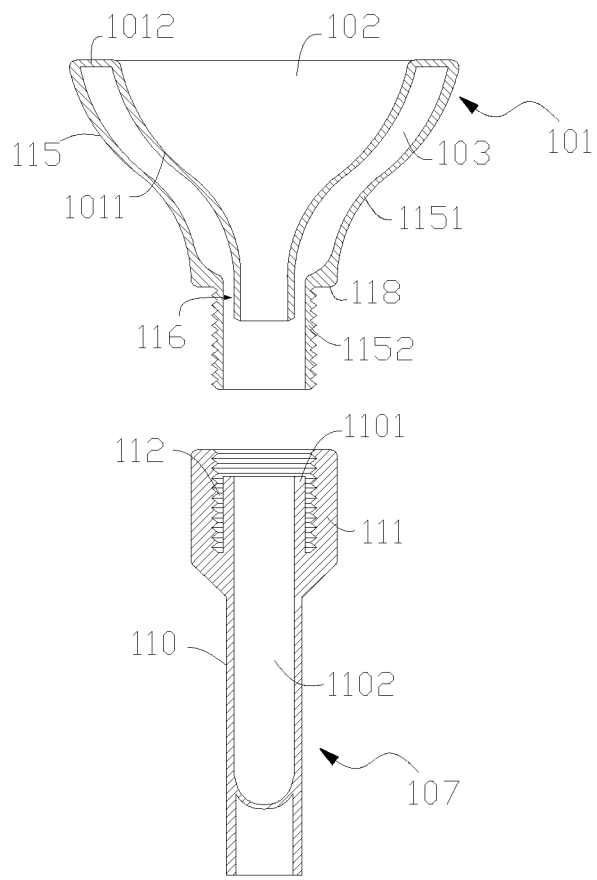
FIG. 15 is an exploded structural schematic diagram of the liquid collecting device provided in an embodiment of the present disclosure.
Figure 16:
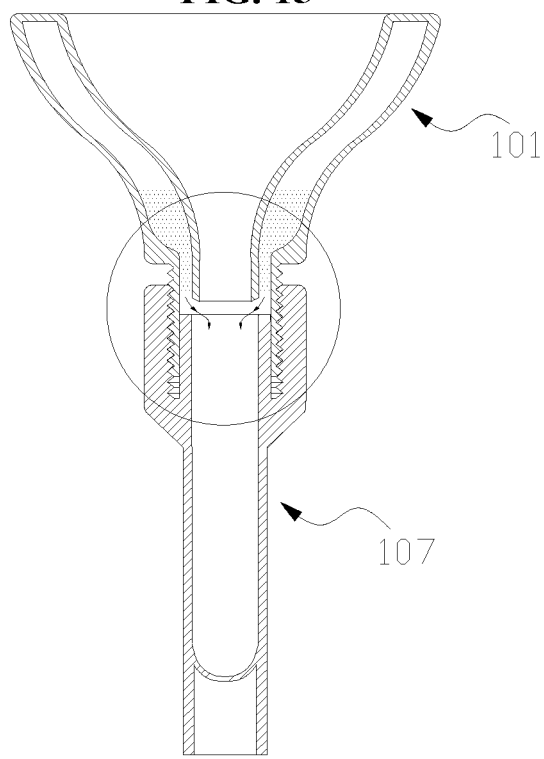
FIG. 16 is an assembled structural schematic diagram of the liquid collecting device provided in an embodiment of the present disclosure.
Figure 17:
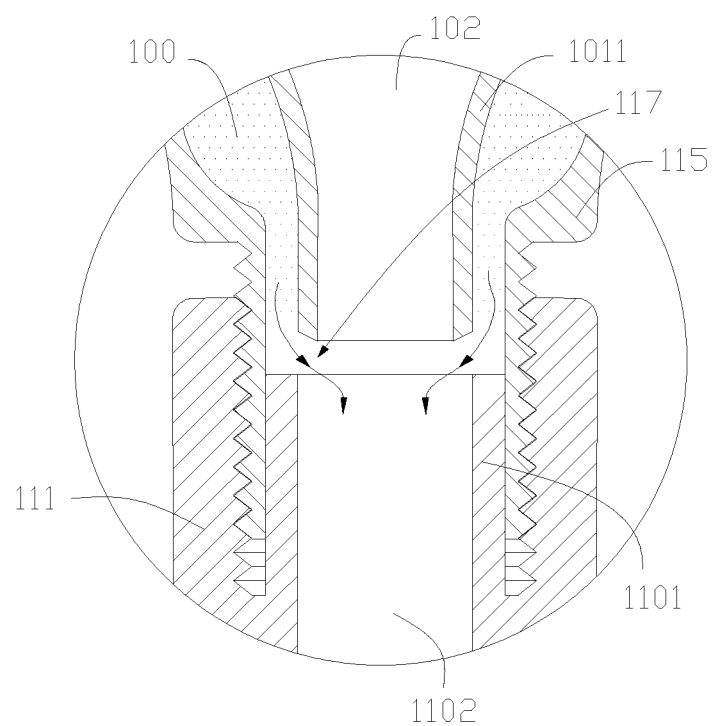
FIG. 17 is a partially enlarged structural schematic diagram of FIG. 16.

In the present disclosure, please referring to FIG. 15-FIG. 17, FIG. 15 shows an exploded structural schematic diagram of a liquid collecting device mentioned in the present disclosure; FIG. 16 shows a structural schematic diagram in which the collecting container 101 and the storing container 107 mentioned in the present disclosure are away from each other such that the liquid outlet 109 is in communication with the accommodating cavity 1102 of the storing container 107; FIG. 17 shows a partially enlarged structural schematic diagram in FIG. 16, wherein two guide lines provided with two arrows in FIG. 17 indicate directions in which the storage liquid 100 flows.

Please referring to FIG. 15 and FIG. 16, the liquid collecting device includes the collecting container 101 and the storing container 107, the collecting container 101 is movably connected to the storing container 107, when the collecting container 101 and the storing container 107 move relatively, the jacket cavity 103 of the collecting container 101 can be communicated with or blocked from the accommodating cavity 1102 of the storing container 107, and when the jacket cavity 103 of the collecting container 101 is blocked from the accommodating cavity 1102 of the storing container 107, the storage liquid 100 stored in the jacket cavity 103 is always located inside the jacket cavity 103, and does not enter the accommodating cavity 1102 of the storing container 107; when the jacket cavity 103 of the collecting container 101 is in communication with the accommodating cavity 1102 of the storing container 107, the storage liquid 100 stored in the jacket cavity 103 flows into the jacket cavity 103, and is mixed with the liquid (e.g., saliva, blood or urine) flowing into the accommodating cavity 1102 of the storing container 107 from the diversion cavity 102 of the collecting container 101.

Please referring to FIG. 15 and FIG. 16, the collecting container 101 includes an inner shell portion 1011, the insertion portion 108, a capping portion 1012 and the outer shell portion 115, the inner shell portion 1011 defines the diversion cavity 102, and two ends of the inner shell portion 1011 along the axial direction of the diversion cavity 102 are both open. In other words, the diversion cavity 102 defined by the inner shell portion 1011 is in a through hole shape, the diversion cavity 102 has the inflow port 104 and the outflow port 105 located at two axial ends thereof, respectively, and an aperture of the inflow port 104 of the diversion cavity 102 is larger than that of the outflow port 105 of the diversion cavity 102. Furthermore, a cross-sectional profile of the diversion cavity 102 perpendicular to the axial direction thereof is circular, and an inner diameter of the diversion cavity 102 gradually decreases in a direction from the inflow port 104 to the outflow port 105, that is, the inner shell portion 1011 is substantially in a funnel shape. The insertion portion 108 is in a cylindrical shape, and optionally, the insertion portion 108 can be formed by extending an end of the inner shell portion 1011 having the outflow port 105 in a linear direction away from the inflow port 104. The capping portion 1012 is in a disc shape, the capping portion 1012 has a circular inner ring and a circular outer ring, and the inner shell portion 1011 is hermetically connected to the inner ring. Specifically, an end portion of the inner shell portion 1011 where the inflow port 104 is located is hermetically connected to the inner ring. The outer shell portion 115 is substantially in a funnel shape, the outer shell portion 115 has a variable-diameter shell section 1151 and a constant-diameter shell section 1152 that are connected, and the variable-diameter shell section 1151 is hermetically connected to the outer ring of the capping portion 1012, an inner diameter of the variable-diameter shell section 1151 gradually decreases from one end close to the capping portion 1012 to the other end, and the constant-diameter shell section 1152 is connected to an end of the variable-diameter shell section 1151 with a smaller diameter. An extending direction of the outer shell portion 115 is consistent with an extending direction of the inner shell portion 1011, and the jacket cavity 103 is formed between the inner wall of the outer shell portion 115 and the outer wall of the inner shell portion 1011. The constant-diameter shell section 1152 is substantially in a cylindrical shape, the constant-diameter shell section 1152 is coaxial with the insertion portion 108, the insertion portion 108 is located inside the constant-diameter shell section 1152, a to-be-sealed region 116 is defined between an outer wall of the insertion portion 108 and an inner wall of the constant-diameter shell section 1152, a liquid outlet 109 communicated with the jacket cavity 103 is defined between the inner wall of the constant-diameter shell section 1152 and an end opening of the insertion portion 108 away from the inner shell portion 1011, the to-be-sealed region 116 can be blocked so as to block the liquid outlet 109 from the jacket cavity 103, and on the contrary, the to-be-sealed region 116 can be opened so as to realize communication between the liquid outlet 109 and the jacket cavity 103. An outer circumferential surface of the constant-diameter shell section 1152 is provided with an external thread, and the outer circumferential surface of the constant-diameter shell section 1152 and an outer circumferential surface of the variable-diameter shell section 1151 jointly form a step structure 118.

It should be noted that the inner shell portion 1011, the capping portion 1012 and the outer shell portion 115 may be integrally molded.

Please referring to FIG. 15 and FIG. 16, the storing container 107 includes the container body 110 and the sleeve-shaped structure 111 sleeved outside the container body 110, the container body 110 has the accommodating cavity 1102 configured to mix the body fluid with the storage liquid 110, the container body 110 has a sealing section 1101 configured to be inserted into the to-be-sealed region 116 so as to block the liquid outlet 109, and the sealing section 1101 is substantially in a cylindrical shape. The sleeve-shaped structure 111 is located outside the sealing section 1101, and protrudes beyond the end portion of the sealing section 1101, the annular groove 112 is defined between the inner circumferential wall of the sleeve-shaped structure 111 and the outer circumferential wall of the container body 110, and the inner circumferential wall of the sleeve-shaped structure 111 is provided with an internal thread.

In use, the collecting container 101 is assembled with the storing container 107. Specifically, the constant-diameter shell section 1152 is inserted into the sleeve-shaped structure 111, and the external thread on the constant-diameter shell section 1152 is threaded with the internal thread on the sleeve-shaped structure 111, so as to realize the threaded connection between the collecting container 101 and the storing container 107. It is set that when the liquid collecting device is assembled and is in a use state, the collecting container 101 is located above the storing container 107, and the whole liquid collecting device is substantially in a vertical state or an inclined state having an included angle with a horizontal plane. During practical assembling, it is set that the storing container 107 is static, and the collecting container 101 is rotated in a first direction so as to realize threaded connection between the storing container 107 and the collecting container 101. In the process of threading and fixing the collecting container 101 with the storing container 107, the constant-diameter shell section 1152 gradually enters the annular groove 112, the sealing section 1101 of the container body 110 is gradually inserted into the to-be-sealed region 116 formed by the constant-diameter shell section 1152 and the insertion portion 108, the inner circumferential wall of the sealing section 1101 is in contact and sealed connection with the outer circumferential wall of the insertion portion 108, the outer circumferential wall of the sealing section 1101 is in contact and sealed connection with the inner circumferential wall of the constant-diameter shell section 1152. In other words, in the process of screwing the collecting container 101 into the storing container 107, the sealing section 1101 is inserted into the to-be-sealed region 116, and blocks the to-be-sealed region 116, finally, the blocking of the liquid outlet 109 is realized, the storage liquid 100 located inside the jacket cavity 103 is sealed inside the jacket cavity 103, and the storage liquid 100 will not enter the accommodating cavity 1102 of the container body 110 through the liquid outlet 109. When a liquid (e.g., saliva, blood or urine) enters the accommodating cavity 1102 of the container body 110 from the diversion cavity 102, the storage liquid 100 inside the jacket cavity 103 needs to be mixed with the liquid inside the container body 110, at which time, it is set that the storing container 107 is static, the collecting container 101 is rotated in a second direction opposite to the first direction, in other words, the operation of unscrewing the collecting container 101 from the storing container 107 is carried out to loosen their connection. Please referring to FIG. 17, in the process of the unscrewing operation, the constant-diameter shell section 1152 gradually gets away from the annular groove 112, and the sealing section 1101 gradually gets away from the to-be-sealed region 116, and since the insertion portion 108 is retracted back into the constant-diameter shell section 1152, when the sealing section 1101 gets away from the to-be-sealed region 116, the separation of the inner circumferential wall of the sealing section 1101 from the outer circumferential wall of the insertion portion 108 is prior to the separation of the outer circumferential wall of the sealing section 1101 from the inner circumferential wall of the constant-diameter shell section 1152. In other words, in the process that the sealing section 1101 gets away from the to-be-sealed region 116, the insertion portion 108 first is separated from the sealing section 1101, a notch 117 is formed between the insertion portion 108 and the sealing section 1101, and when the liquid outlet 109 is opened, the storage liquid 100 inside the jacket cavity flows out through the liquid outlet 109 and enters the accommodating cavity 1102 of the container body 110 at the notch 117, while the sealing section 1101 and the constant-diameter shell section 1152 can still maintain a sealed state therebetween, the storage liquid will not flow out between the outer circumferential wall of the sealing section 1101 and the inner circumferential wall of the constant-diameter shell section 1152, the storage liquid 100 will not enter the annular groove 112, then it is not easy to cause waste of the storage liquid 100, and it is not easy to cause the situation that the storage liquid 100 pollutes the annular groove 112. So far, after the storage liquid 100 enters the accommodating cavity 1102 of the container body 110 through the liquid outlet 109, the storage liquid 100 is mixed with the liquid located inside the container of the container body 110, completing the liquid collecting operation.

It should be noted that, during the process of the threaded fixed connection between the collecting container 101 and the storing container 107, an end surface of the sleeve-shaped structure 111 can abut against the step structure 118 formed by the variable-diameter shell section 1151 and the constant-diameter shell section 1152, so as to remind an operator that the sealing section 1101 is already located in the to-be-sealed region 116, at which time the liquid outlet 109 is blocked.

The present disclosure further provides a liquid collecting device, and in the present disclosure, another implementation scheme, in which the jacket cavity 103 is communicated with or disconnected from the accommodating cavity 1102 of the storing container 107 through relative rotation between the storing container 107 and the collecting container 101, is described, and the same contents as those of the liquid collecting device mentioned in the preceding will not be repeated.

Figure 4:
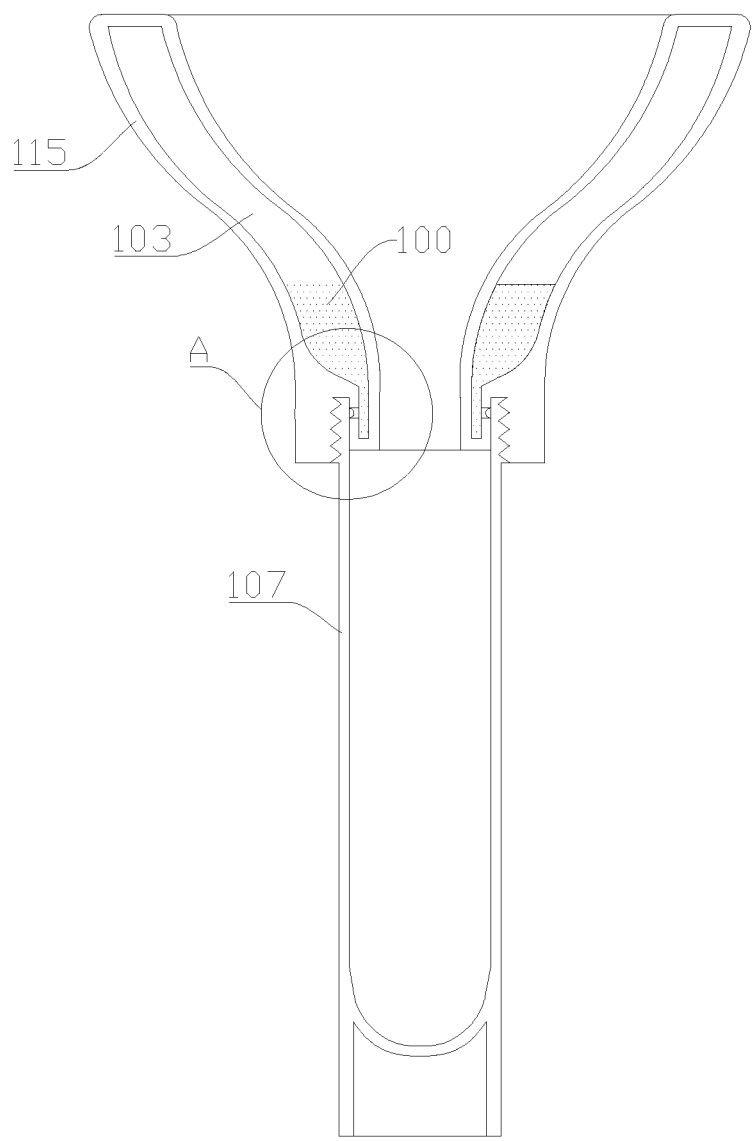
FIG. 4 is a schematic diagram (cutaway view) of another modified structure of the liquid collecting device provided in an embodiment of the present disclosure.
Figure 5:
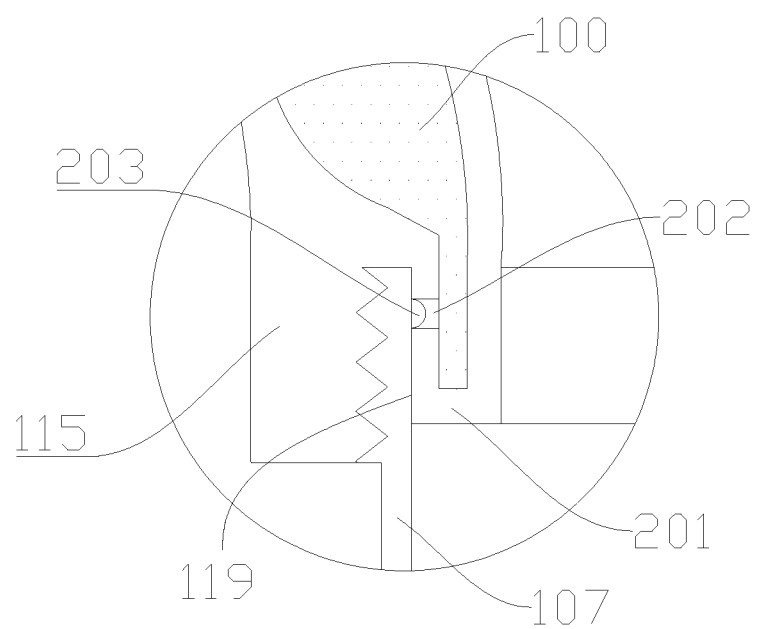
FIG. 5 is a partially enlarged schematic diagram of part A in FIG. 4.

Referring to what is shown in FIG. 4 and FIG. 5, in the present disclosure, the number of the jacket cavity 103 is one; the outer shell portion 15 of the collecting container 101 has an internal thread, and the storing container 107 has an external thread that fits the internal thread; the insertion portion 108 of the collecting container 101 includes a bending section which can be a U-shaped structure 201, an annular groove 112 is formed between the outer shell portion 115 of the collecting container 101 and one side surface of the U-shaped structure 201, the liquid outlet 109 of each jacket cavity 103 is provided on a side surface of the U-shaped structure 201, and the liquid outlet 109 of the jacket cavity 103 is a round hole 202; on an inner wall of a top end of the storing container 107, there is a spherical protrusion 203 corresponding to the position of the liquid outlet 109 of each jacket cavity 103, and the spherical protrusion 203 can block the round hole 202. When the external thread on the storing container 107 cooperates with the internal thread on the outer shell portion 115, the top end of the storing container 107 extends into the annular groove 112, and when one of the storing container 107 and the collecting container 101 is rotated relatively to the other and rotated to set positions, the spherical protrusion 203 blocks the liquid outlet 109 of the jacket cavity 103. In use, when the collecting container 101 is gradually separated from the storing container 107, the spherical protrusion 203 gets away from the position of the round hole 202, and the storage liquid 100 in the jacket cavity 103 flows out through the liquid outlet 109, and flows into the storing container 107 from the gap 119 between a side surface of the U-shaped structure 201 and the inner wall of the storing container 107. It should be noted that, in order to realize that the spherical protrusion 203 can well block the round hole 202, a maximum value of a cross-sectional diameter of the spherical protrusion 203 is greater than an aperture of the round hole 202, and the spherical protrusion 203 may be made of silica gel or rubber, so that the spherical protrusion 203 can be deformed, thereby the round hole 202 can be better sealed, and further normal rotation between the storing container 107 and the collecting container 101 can be ensured. In addition, whether one of the collecting container 101 and the storing container 107 is rotated relatively to the other to the set positions or not can be determined by arranging alignment lines thereon in advance, so that when the alignment lines on the collecting container 101 and the storing container 107 are aligned to each other, the spherical protrusion 203 can block the round hole 202, and an operator is reminded that the collecting container 101 and the storing container 107 have been located in the set positions; in addition, the collecting container 101 or the storing container 107 further can be made of a transparent material for easy observation, wherein the transparent material can be transparent glass or transparent plastic.

The present disclosure further provides a liquid collecting device, and another implementation scheme, in which the jacket cavity 103 is communicated with or disconnected from the accommodating cavity 1102 of the storing container 107, is described, and in the present disclosure, the same contents as those of the liquid collecting device mentioned in the preceding will not be repeated.

Figure 6:
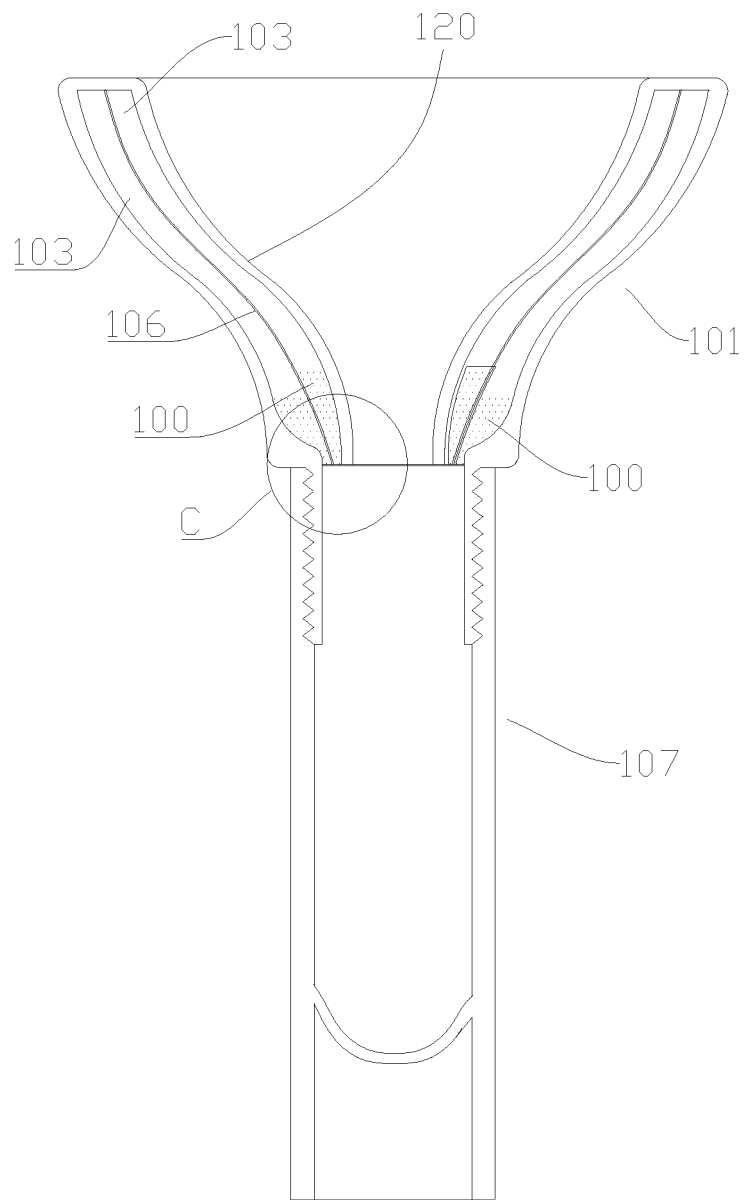
FIG. 6 is a schematic diagram (cutaway view) of another modified structure of the liquid collecting device provided in an embodiment of the present disclosure.
Figure 7:
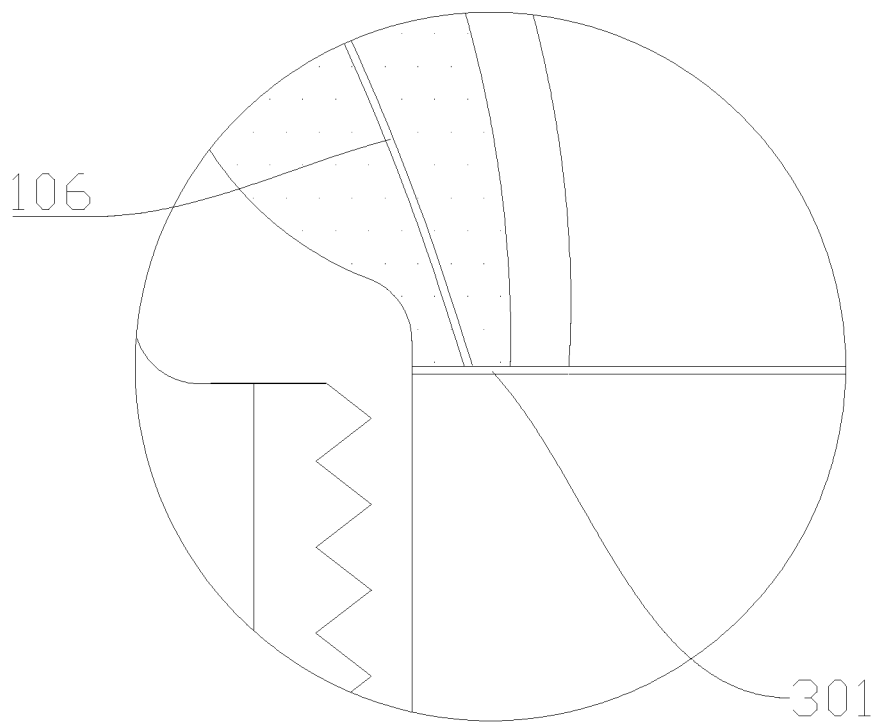
FIG. 7 is a partially enlarged schematic diagram of part C in FIG. 6.
Figure 11:
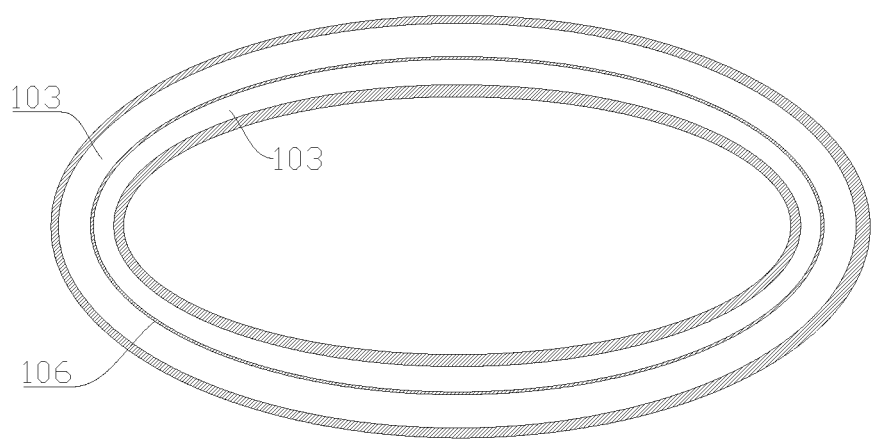
FIG. 11 is a radial sectional view of the liquid collecting device shown in FIG. 6.
Figure 12:
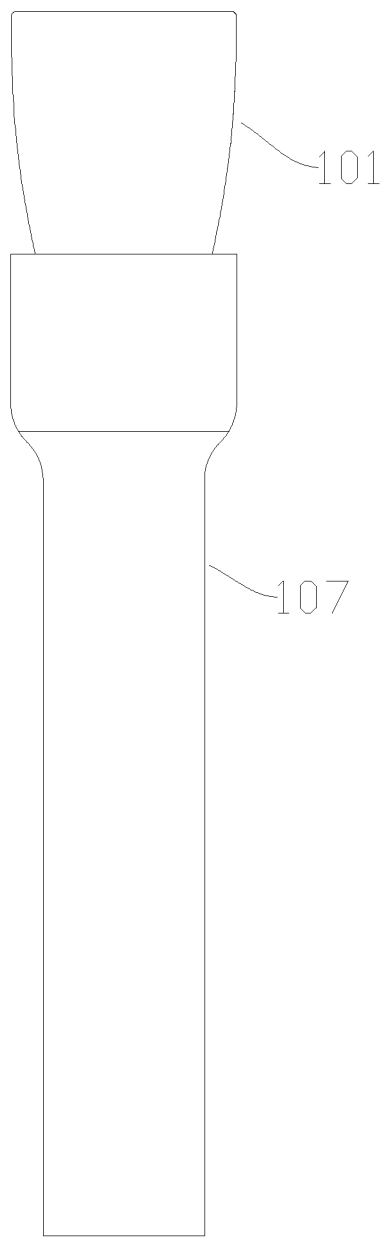
FIG. 12 is a basic structural schematic diagram of the liquid collecting device provided in an embodiment of the present disclosure.
Figure 13:
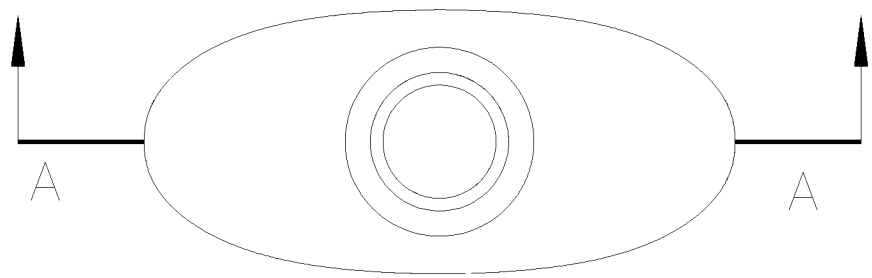
FIG. 13 is a top view of FIG. 12.
Figure 14:
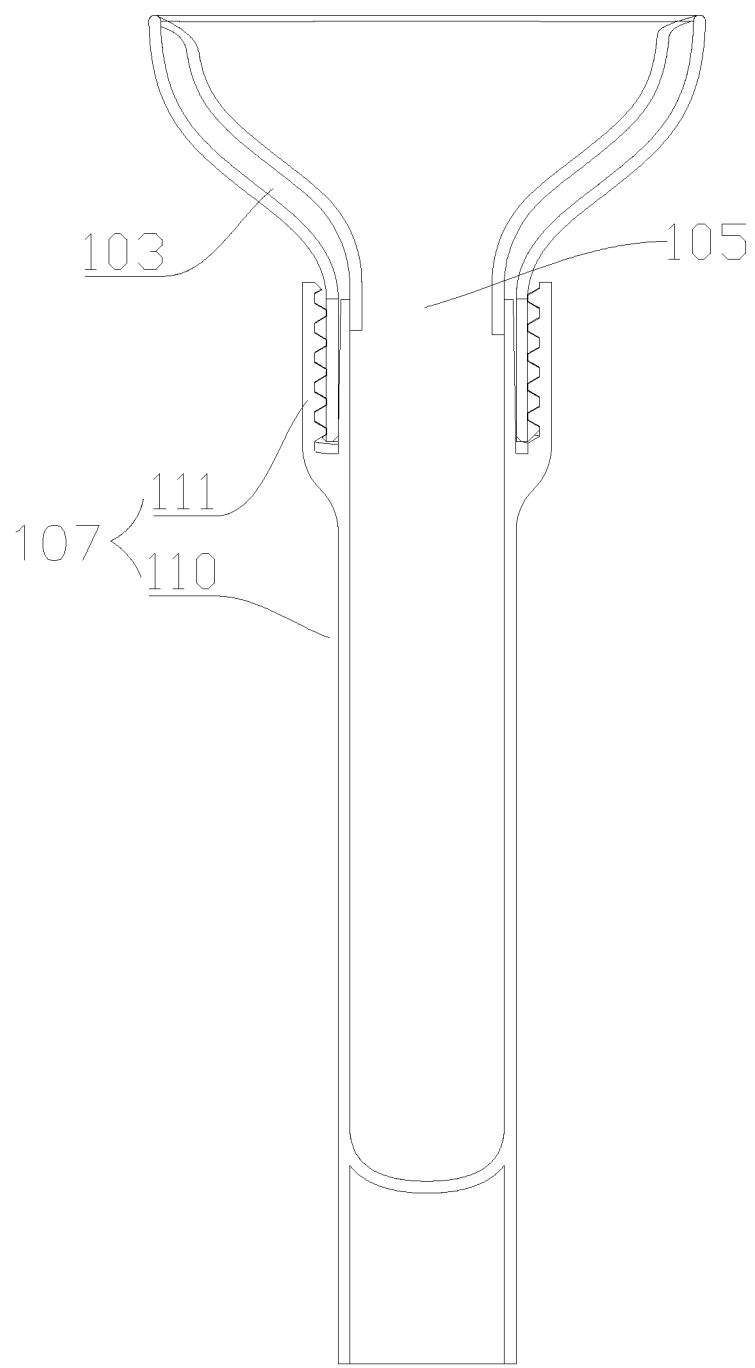
FIG. 14 is a cutaway view along line A-A in FIG. 13.

Referring to what is shown in FIG. 6, FIG. 7 and FIG. 11, in this embodiment, the number of the jacket cavities 103 is plural, and the plurality of jacket cavities 103 are separated by an isolation layer 106. Optionally, the length of the isolation layer 106 extends along the axial direction of the diversion cavity 102, the isolation layer 106 is in a cylindrical shape (skirt like shape or flared shape), and after the isolation layer 106 separates the plurality of jacket cavities 103 from each other, the plurality of jacket cavities 103 are arranged along a radial direction of the diversion cavity 102. The liquid outlet 109 of each jacket cavity 103 is close to the outflow port 105 of the collecting container 101, and far away from the inflow port 104 of the collecting container 101, and in use, the storage liquid 100 in the jacket cavity 103 can be allowed to flow out by opening up the liquid outlet 109. Meanwhile, the isolation layer 106 extends along the axial direction of the diversion cavity 102, so that on one hand, the volume of the jacket cavity 103 can be increased as much as possible, and on the other hand, it facilitates arranging a plurality of liquid outlets 109 of the plurality of jacket cavities 103 close to the outflow port 105 of the collecting container 101.

In the present disclosure, the plurality of jacket cavities 103 are sequentially sleeved from inside to outside along the radial direction of the diversion cavity 102, a wall surface of an innermost jacket cavity 103 is opposite to an inner wall surface of the diversion cavity 102, that is, the innermost jacket cavity 103 is isolated from the diversion cavity 102 by a chamber separation layer 120, one surface of the chamber separation layer 120 is the wall surface of the jacket cavity 103, and the other opposite surface of the chamber separation layer 120 is the inner wall surface of the diversion cavity 102. Such structural design can increase the capacity of the jacket cavity 103, and facilitate storing more storage liquid.

Specifically, in the present disclosure, the number of the jacket cavities being 2 is taken as an example to make specific illustration. The liquid collecting device further includes a sealing film(s) 301 connected to the jacket cavities 103, and configured to seal the storage liquids 100 within the jacket cavities 103, respectively. Specifically, the sealing film 301 may be aluminum foil film, and the aluminum foil film is fixed at the plurality of liquid outlets 109 corresponding to the plurality of jacket cavities 103, respectively, in a hot pressing manner, so as to seal the plurality of liquid outlets 109, such that the storage liquids 100 are sealed in the jacket cavities 103, respectively, realizing the sealing between the jacket cavities 103 and the accommodating cavities 1102 of the storing container 107. It should be noted that the number of the jacket cavity 103 also may be 1 (see what is shown in FIG. 8), or 3~6; and when the number of the jacket cavities is 3 or more, the isolation layer 106 is at least in two, and at least two cylindrical isolation layers 106 are provided in a sleeved manner.

In the present disclosure, by providing a plurality of jacket cavities 103, the liquid collecting device can store a plurality of storage liquids 100 of the same type or the storage liquids 100 of different types at the same time. In other words, when the number of the jacket cavity 103 is two or more, the types of the storage liquids 100 stored in the two or more jacket cavities 103, respectively, may be the same, or the types of the storage liquids 100 stored in any two jacket cavities 103 of the two or more jacket cavities 103 may be different, so as to store a plurality of types of storage liquids 100. The collecting container 101 provided in the present disclosure has dual functions of diverting the liquid and storing the storage liquid 100; in addition, when a plurality of different storage liquids 100 are stored, the storage liquids 100 of various reagents can be prevented from being mixed in advance before use, and the storage liquids 100 of a plurality of types do not react chemically before mixing, thus protecting respective terms of validity of the storage liquids 100 to the maximum extent.

In the present disclosure, the collecting container 101 has the external thread, and the storing container 107 has the internal thread that fits the external thread; the collecting container 101 is in threaded connection with the storing container 107, and after the sealing film 301 of the liquid outlet 109 of the jacket cavity 103 is torn off, communication between the jacket cavity 103 and the accommodating cavity 1102 of the storing container 107 is realized, then the storage liquid 100 can enter the storing container 107.

In use, the collecting container 101 is first inverted, to enable the sealing film 301 to be arranged upwards, then the sealing film 301 at the liquid outlet 109 of the jacket cavity 103 is torn off, then the collecting container 101 is connected to the storing container 107 in a threaded manner, thereafter the collecting container 101 and the storing container 107 that have been connected are integrally turned over, such that the collecting container 101 is located above the storing container 107. In other words, the storing container 107 is located below the collecting container 101, such that the storage liquid 100 enters the accommodating cavity 1102 of the storing container 107 from the jacket cavity 103.

The present disclosure further provides a liquid collecting device, and in the present disclosure, the same contents as those of the liquid collecting device mentioned in the preceding will not be repeated.

Referring to what is shown in FIG. 1, in the present disclosure, a sealing separator 401 is installed in the storing container 107. A blocking hole 404 is provided in the sealing separator 401; the sealing separator 401 divides the accommodating cavity 1102 of the storing container 107 into an upper sealed cavity 405 and a lower sealed cavity 406, and the storage liquid 100 is pre-stored in the lower sealed cavity 406; the collecting container 101 is connected to a connecting rod 402, an end portion of the connecting rod 402 is connected to a sealing block 403, and the sealing block 403 can be inserted into the blocking hole 404 of the sealing separator 401, so as to block the blocking hole 404 of the sealing separator 401, thereby sealing the storage liquid 100 in the lower sealed cavity 406.

A method of using the liquid collecting device is as follows:

spitting saliva into the collecting container 101; loosening the connection between the collecting container 101 and the storing container 107, so as to open the blocking hole of the sealing separator 401, and realize communication between the upper sealed cavity 405 and the lower sealed cavity 406, wherein saliva flows from the upper sealed cavity 405 into the lower sealed cavity 406 to be mixed with the storage liquid 100 in the lower sealed cavity 406, and finally, completely unscrewing the collecting container 101, and plugging a sealing plug into the container mouth of the storing container 107.

It should be noted that the liquid collecting device mentioned in the present disclosure can be configured to collect a liquid such as a body fluid, and store the collected liquid after being mixed with the storage liquid 100.

To sum up, the liquid collecting device provided in the present disclosure can realize flow of the storage liquid 100 into the accommodating cavity 1102 of the storing container 107 and mixing with the body fluid located inside the accommodating cavity 1102 of the storing container 107 during the process of unscrewing the collecting container 101 located in the upper portion, without one more step by a user. The liquid collecting device can realize the separation of various reagents (such as unstable enzymes with high activity) before mixing, so that the various reagents will not be mixed in advance, and will not react chemically, protecting respective terms of validity of the reagents to the maximum extent, and meanwhile further having the convenience of mixing multiple reagents after sampling. No complicated reagent pouring is needed, and operation steps of customers are controlled to be minimum. In addition, the liquid collecting device mentioned in the present disclosure can be configured to collect the body fluid such as saliva or urine of a human body or an animal, and use the collected liquid as a sample, and meanwhile, realize mixing of a reagent (e.g., the storage liquid 100) with the sample through a convenient operation. In addition, in the present disclosure, the storage liquid 100 in the jacket cavity 103 can be sealed by slope surfaces connected by threads, the collecting container 101 and the storing container 107 are connected by a threaded connection structure, a protrusion is provided on a mating surface of the threads, sealing of the liquid inside the jacket cavity 103 is realized after the collecting container 101 and the storing container 107 are screwed down, and releasing of the liquid inside the jacket cavity 103 is realized after the connection between collecting container 101 and the storing container 107 is loosened via unscrewing; the sealing of the storage liquid 100 inside the jacket cavity 103 can also be realized by a scheme of slant extrusion sealing. The collecting container 101 and the storing container 107 are sealed from each other in a screwed state; in an unscrewed state, the jacket cavity 103 is communicated with the storing container 107 so as to release the storage liquid 100.

Finally, it should be noted that various embodiments mentioned above are merely used to illustrate the technical solutions of the present disclosure, rather than limiting the same, and for one skilled in the art, various modifications and variations can be made to the present disclosure. Any amendments, equivalent replacements, improvements and so on, within the spirit and principle of the present disclosure, should be covered within the scope of protection of the present disclosure.

INDUSTRIAL APPLICABILITY

To sum up, the present disclosure provides a liquid collecting device, which is convenient in operation, high in efficiency, and low in cost.

What is claimed is:

1. A liquid collecting device, comprising a collecting container, wherein the collecting container is provided with a diversion cavity for diverting a body fluid collected;
at least one jacket cavity configured to store a storage liquid is provided on a wall of the collecting container, the at least one jacket cavity is arranged around the diversion cavity, and the at least one jacket cavity extends along an axial direction of the diversion cavity, and a cross section of each of the at least one jacket cavity is annular; and
the diversion cavity has an inflow port and an outflow port, and an aperture of the inflow port is larger than that of the outflow port.

2. The liquid collecting device according to claim 1, wherein an inner diameter of the diversion cavity gradually decreases in a direction from the inflow port to the outflow port.

3. The liquid collecting device according to claim 1, wherein the number of the at least one jacket cavity is plural, and the plurality of jacket cavities are independent from each other.

4. The liquid collecting device according to claim 3, wherein the liquid collecting device further comprises at least one isolation layer, the plurality of jacket cavities are separated by the at least one isolation layer, and a length of each of the at least one isolation layer extends along an axial direction of the diversion cavity; and each of the at least one isolation layer is in a cylindrical shape.

5. The liquid collecting device according to claim 4,
wherein the plurality of jacket cavities are sequentially sleeved from inside to outside along a radial direction of the diversion cavity, a wall surface of an innermost one of the jacket cavities is opposite to an inner wall surface of the diversion cavity,
wherein the innermost one of the jacket cavities is isolated from the diversion cavity by a chamber separation layer.

6. The liquid collecting device according to claim 1, wherein the liquid collecting device further comprises a storing container, and the storing container is connected to the collecting container, so that the diversion cavity is communicated with an accommodating cavity of the storing container.

7. The liquid collecting device according to claim 6, wherein the number of the at least one jacket cavity is 1.

8. The liquid collecting device according to claim 7, wherein the storing container is movably connected to the collecting container, such that the jacket cavity is communicated with or disconnected from the accommodating cavity of the storing container.

9. The liquid collecting device according to claim 8, wherein the storing container is rotationally connected to the collecting container, such that the jacket cavity is communicated with or disconnected from the accommodating cavity of the storing container.

10. The liquid collecting device according to claim 9, wherein the storing container is in threaded connection with the collecting container, such that the jacket cavity is communicated with or disconnected from the accommodating cavity of the storing container.

11. The liquid collecting device according to claim 6, wherein the collecting container has an insertion portion configured to be inserted into the storing container;
the insertion portion and an inner wall of the storing container have a communicated state therebetween, in which the storage liquid stored in the jacket cavity is enabled to flow into the accommodating cavity of the storing container;

the insertion portion and the inner wall of the storing container further have a disconnected state therebetween, in which the storage liquid is sealed in the jacket cavity.

12. The liquid collecting device according to claim 7, wherein an inner circumferential wall of the insertion portion is configured to form a part of a wall surface of the diversion cavity;

an outer circumferential wall of the insertion portion is configured to form a part of a wall surface of the jacket cavity;

the outer circumferential wall of the insertion portion is attached to the inner wall of the storing container so as to realize sealing.

13. The liquid collecting device according to claim 7, wherein the collecting container further comprises an inner shell portion, a capping portion and an outer shell portion, an inner wall of the inner shell portion defines the diversion cavity, and an end of the inner shell portion forming the outflow port is connected to the insertion portion;

the capping portion is annular, an end of the inner shell portion forming the inflow port is connected to an inner ring of the capping portion, the outer shell portion is connected to an outer ring of the capping portion, an extending direction of the outer shell portion is consistent with an extending direction of the inner shell portion; and an end of the outer shell portion away from the capping portion protrudes beyond the insertion portion; and the outer shell portion, the capping portion and the inner shell portion jointly define the jacket cavity.

14. The liquid collecting device according to claim 13, wherein the outer shell portion comprises a variable-diameter shell section and a constant-diameter shell section, an inner diameter of the variable-diameter shell section gradually decreases from one end close to the capping portion to the other end, an end of the constant-diameter shell section is connected to an end of the variable-diameter shell section away from the capping portion, an end of the constant-diameter shell section away from the variable-diameter shell section protrudes beyond the insertion portion, and a to-be-sealed region is formed between the constant-diameter shell section and the variable-diameter shell section;

the storing container is movable relative to the collecting container, such that the storing container is located in the to-be-sealed sealed region so as to block the jacket cavity from the accommodating cavity of the storing container, and that the storing container is separated from the to-be-sealed sealed region so as to make the jacket cavity communicated with the accommodating cavity of the storing container.

15. The liquid collecting device according to claim 14, wherein the storing container comprises a container body and a sleeve-shaped structure sleeved outside the container body, an annular grove configured to accommodate the constant-diameter shell section is formed between the container body and the sleeve-shaped structure;

the constant-diameter shell section is in threaded connection with the sleeve-shaped structure, the container body is configured to move to be located in the to-be-sealed sealed region so as to block the jacket cavity from the accommodating cavity of the storing container, or move to be separated from the to-be-sealed sealed region so as to communicate the jacket cavity with the accommodating cavity of the storing container.

16. The liquid collecting device according to claim 15, wherein the liquid collecting device further comprises a sealing element, and the sealing element is provided between the container body and the insertion portion, and configured to seal a gap between the container body and the insertion portion.

17. The liquid collecting device according to claim 14, wherein the insertion portion is provided with a bending section that is bent away from the diversion cavity, the bending section is provided with a liquid outlet, the liquid outlet is capable of being opened or closed by the storing container, and when the liquid outlet is opened by the storing container, the jacket cavity, the liquid outlet and the accommodating cavity of the storing container are communicated in sequence; and when the liquid outlet is closed by the storing container, the jacket cavity is blocked from the accommodating cavity of the storing container.

18. The liquid collecting device according to claim 17, wherein the storing container is provided with a spherical protrusion configured to block the liquid outlet.

19. The liquid collecting device according to claim 1, wherein the liquid collecting device further comprises a sealing film attached to the collecting container, and the sealing film is configured to seal the storage liquid in the at least one jacket cavity.

20. The liquid collecting device according to claim 6, wherein a sealing separator is installed in the storing container;

a blocking hole is provided in the sealing separator;

the sealing separator divides the accommodating cavity of the storing container into an upper sealed cavity and a lower sealed cavity, the upper sealed cavity is configured to be communicated with the diversion cavity, and the storage liquid is pre-stored in the lower sealed cavity;

the collecting container is connected to a connecting rod, an end portion of the connecting rod is connected to a sealing block, and the sealing block is capable of being inserted into the blocking hole, so as to block the blocking hole.

* * * * *